(12) United States Patent
Cooper et al.

(10) Patent No.: US 6,239,140 B1
(45) Date of Patent: May 29, 2001

(54) COMPOUNDS USEFUL FOR INHIBITION OF FARNESYL PROTEIN TRANSFERASE

(75) Inventors: Alan B. Cooper, West Caldwell; Ronald J. Doll, Maplewood; Anil K. Saksena, Upper Montclair; Viyyoor M. Girijavallabhan, Parsippany, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/094,689

(22) Filed: Jun. 15, 1998

Related U.S. Application Data

(60) Provisional application No. 60/049,859, filed on Jun. 17, 1997.

(51) Int. Cl.[7] .................... C07D 487/00; C07D 471/00; A61K 31/44
(52) U.S. Cl. .............................. 514/290; 546/93
(58) Field of Search ................ 546/93; 514/290

(56) References Cited

U.S. PATENT DOCUMENTS

| | | |
|---|---|---|
| 4,826,853 | 5/1989 | Piwinski et al. .................... 514/290 |
| 5,089,496 | 2/1992 | Piwinski et al. .................... 514/253 |
| 5,151,423 | 9/1992 | Piwinski et al. .................... 514/254 |
| 5,393,890 | 2/1995 | Syoji et al. ............................. 546/80 |
| 5,464,840 | 11/1995 | Ting et al. ............................ 514/277 |
| 5,561,117 | 10/1996 | Wong et al. .......................... 514/291 |
| 5,661,152 | 8/1997 | Bishop et al. ........................ 514/254 |
| 5,672,611 | 9/1997 | Doll et al. ............................ 514/325 |
| 5,684,013 | 11/1997 | Afonso et al. ....................... 514/254 |
| 5,696,121 | 12/1997 | Bishop et al. ........................ 514/254 |
| 5,700,806 | 12/1997 | Doll et al. ............................ 514/290 |
| 5,703,090 | 12/1997 | Afonso et al. ....................... 514/290 |
| 5,712,280 | 1/1998 | Doll et al. ............................ 514/253 |
| 5,714,609 | 2/1998 | Bishop et al. ............................ 546/93 |
| 5,719,148 | 2/1998 | Bishop et al. .................... 514/228.2 |
| 5,721,236 | 2/1998 | Bishop et al. ........................ 514/255 |
| 5,728,703 | 3/1998 | Bishop et al. ........................ 514/254 |

FOREIGN PATENT DOCUMENTS

| | | |
|---|---|---|
| 0270818 | 6/1988 | (EP) . |
| 396083 | 11/1990 | (EP) . |
| WO93/20080 | 10/1993 | (WO) . |
| WO95/10515 | 4/1995 | (WO) . |
| WO95/10516 | 4/1995 | (WO) . |
| WO95/15949 | 6/1995 | (WO) . |
| WO96/30018 | 10/1996 | (WO) . |
| WO96/30362 | 10/1996 | (WO) . |
| WO96/30363 | 10/1996 | (WO) . |
| WO96/31477 | 10/1996 | (WO) . |
| WO96/31478 | 10/1996 | (WO) . |
| WO97/23478 | 7/1997 | (WO) . |

OTHER PUBLICATIONS

Bishop et al., The Journal of Biological Chemistry, vol. 270, No. 15, pp.30611–30618 (1995).
Njoroge et al., Bioorganic & Medicinal Chemistry Letters, vol. 6, No. 24, pp.2977–2982 (1996).
Villani, F.J. et al., Journal of Medicinal Chemistry vol. 15, No. 7, p. 750–754 (1972).

*Primary Examiner*—Alan L. Rotman
(74) *Attorney, Agent, or Firm*—Henry C. Jeanette

(57) ABSTRACT

Novel compounds of the formula:

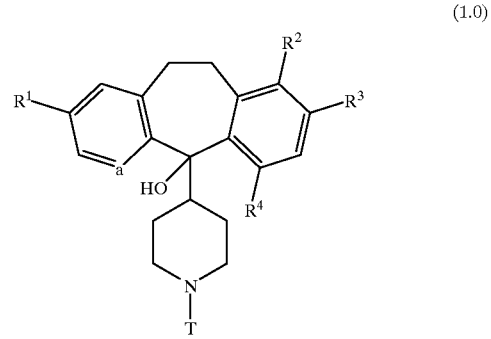

(1.0)

or a pharmaceutically acceptable salt or solvate thereof, wherein:

a represents N or NO⁻;

$R^1$ and $R^3$ are the same or different and each represents halo;

$R^2$ and $R^4$ are the same or different and each is selected from H and halo, provided that at least one of $R^2$ and $R^4$ is H;

T is a substituent selected from $SO_2R$ or:

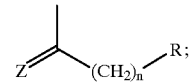

Z is O or S;

n is zero or an integer from 1 to 6;

R is alkyl, aryl, arylalkyl, heteroaryl, heteroarylalkyl, cycloalkyl, heterocycloalkyl, or $N(R^5)_2$;

$R^5$ is H, alkyl, aryl, heteroaryl or cycloalkyl.

Also disclosed are methods of inhibiting farnesyl protein transferase and methods for treating tumor cells.

4 Claims, No Drawings

COMPOUNDS USEFUL FOR INHIBITION OF FARNESYL PROTEIN TRANSFERASE

REFERENCE TO RELATED APPLICATIONS

This application claims the benefit of U.S. Provisional Application No. 60/049,859 filed Jun. 17, 1997.

BACKGROUND

WO 95/10516, published Apr. 20, 1995 discloses tricyclic compounds useful for inhibiting farnesyl protein transferase.

In view, of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds useful for the inhibition of farnesyl protein transferase (FPT). The compounds of this invention are represented by the formula:

(1.0)

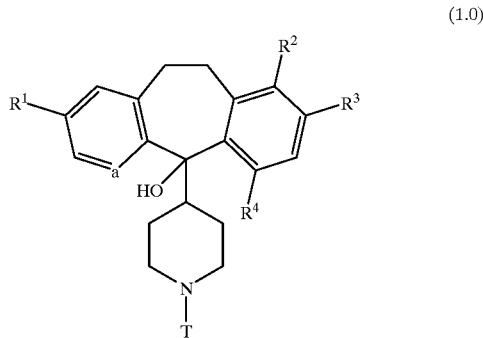

or a pharmaceutically acceptable salt or solvate thereof, wherein:
 a represents N or NO$^-$;
 $R^1$ and $R^3$ are the same or different and each represents halo;
 $R^2$ and $R^4$ are the same or different and each is selected from H and halo, provided that at least one of $R^2$ and $R^4$ is H;
 T is a substituent selected from SO$_2$R or;

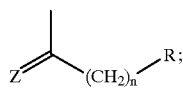

Z is O or S;
 n is zero or an integer from 1 to 6;
 R is alkyl, aryl, arylalkyl, heteroaryl, heteroarylalkyl, cycloalkyl, heterocycloalkyl, or N($R^5$)$_2$;
 $R^5$ is H, alkyl, aryl, heteroaryl or cycloalkyl.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount of the compounds of formula 1.0. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of the tricyclic compounds, described herein, to a mammal (e.g., a human) in need of such treatment. In particular, this invention provides a method for inhibiting or treating the growth of tumors expressing an activated Ras oncogene by the administration of an effective amount of the compounds of formula 1.0. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid folmcular cancer, myelodysplastic syndrome (MDS), bladder carcinoma, epidermal carcinoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of a compound of formula 1.0 to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The compounds of formula 1.0 useful in the methods of this invention inhibit or treat the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:
 MH$^+$-represents the molecular ion plus hydrogen of the molecule in the mass spectrum;

Et (or ET)-represents ethyl (C$_2$H$_5$);

alkyl-represents straight and branched carbon chains that contain from one to twenty carbon atoms, preferably one to six carbon atoms;

halo-represents fluoro, chloro, bromo and iodo;

cycloalkyl-represents saturated carbocyclic rings branched or unbranched of from 3 to 20 carbon atoms, preferably 3 to 7 carbon atoms;

heterocycloalkyl-represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —NR$^9$— (wherein R$^9$ can be, for example, —C(O)N(R$^{10}$)$_2$, —CH$_2$C(O)N(R$^{10}$)$_2$, —SO$_2$R$^{10}$, —SO$_2$N (R$^{10}$)$_2$, —C(O)R$^{11}$, —C(O)—O—R$^{11}$, alky, amyl, aralkyl, cycloalkyl, heterocycloalkyl or heteroaryl; each R$^{10}$ independently represents H, alkyl, aryl, or aralkyl (e.g., benzyl); and R$^{11}$ is alkyl, aryl, aralkyl, heteroaryl or heterocycoalkyl)—(suitable heterocycloalkyl groups include 2-or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, etc. —with preferred heterocycloalkyl groups being 2-, 3- or 4-piperidinyl substituted with R$^{10}$ on the piperidinyl nitrogen);

aryl (including the aryl portion of aryloxy and aralkyl)-represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alky, hydroxy, alkoxy, phenoxy, CF$_3$, amino, alkylamino, diallylamino, —COOR$^{11}$ or —NO$_2$ (wherein R$^{11}$ is H, alkyl, aryl, heteroaryl or cycloalkyl); and heteroaryl-represents cyclic groups, optionally substituted with R$^3$ and R$^4$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., triazolyl, 2-, 3- or 4-pyridyl or pyridyl N-oxide (optionally substituted with R$^{11}$ as defined above), wherein pyridyl N-oxide can be represented as:

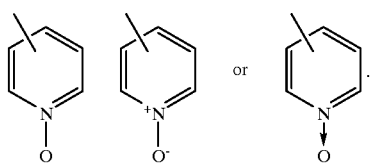

The following solvents and reagents are referred to herein by the abbreviations indicated: ethanol (EtOH); methanol (MeOH); acetic acid (HOAc or AcOH); ethyl acetate (EtOAc); N,N-dimethyl-formamide (DMF); trifluoroacetic acid (TFA); trifluoroacetic anhydride (TFAA); 1-hydroxybenzotriazole (HOBT); 1-(3-dimethylaminopropyl)-3-ethyl carbodiimide hydrochloride (DEC); diisobutylaluminum hydride(DIBAL); and 4-methylmorpholine (NMM).

The positions in the tricyclic ring system are:

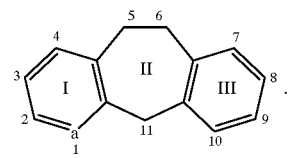

Those skilled in the art will also appreciate that the S and R stereochemistry for the C-11 position of the tricyclic ring is as follows:

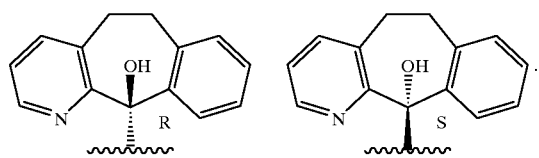

Preferred halo atoms for R$^1$, R$^2$, R$^3$, and R$^4$ in formula 1.0 are selected from: Br, Cl or I, with Br and Cl being preferred.

Compounds of formula 1.0 include compounds of the formula:

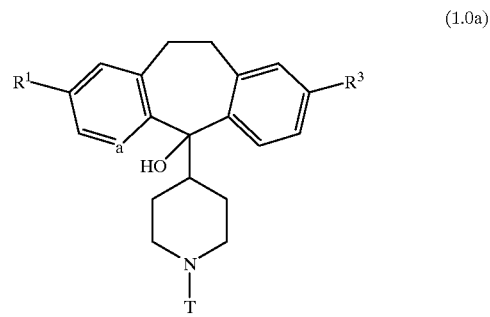

(1.0a)

wherein R$^1$ and R$^3$ are the same or different halo and a and T are as defined above. Preferably, for these dihalo compounds, R$^1$ and R$^3$ are independently selected from Br or Cl, and more preferably R$^1$ is Br and R$^3$ is Cl.

Compounds of formula 1.0 include compounds of formulas 1.1 and 1.2:

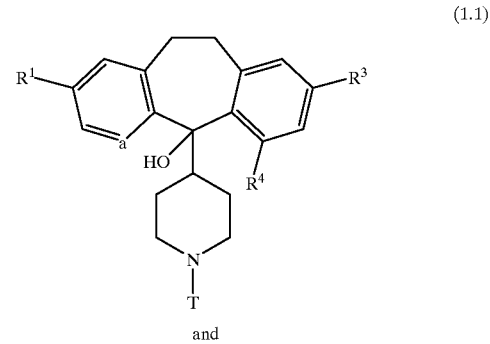

(1.1)

and

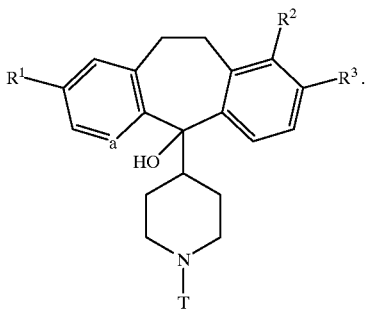

(1.2)

wherein $R^1$, $R^3$ and $R^4$ in formula 1.1 are halo, and $R^1$, $R^2$ and $R^3$ in formula 1.2 are halo. Compounds of formula 1.1 are preferred.

Preferably, in formula 1.1, $R^1$ is Br, $R^3$ is Cl, and $R^4$ is halo. More preferably, in formula 1.1, $R^1$ is Br, $R^3$ is Cl, and $R^4$ is Br.

Preferably, in formula 1.2, $R^1$ is Br, $R^2$ is halo, and $R^3$ is Cl. More preferably, in formula 1.1, $R^1$ is Br, $R^2$ is Br, and $R^3$ is Cl.

Also, preferably, for the compounds of this invention, substituent a in Ring I represents N.

T is preferably —SO$_2$methyl or a group

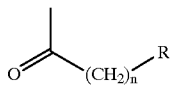

wherein R Is a 3-pydinyl N-oxide, 4-pyridinyl N-oxide, 4-piperdinyl, 3-piperdinyl or 3-pyrrolidinyl group, wherein the 4-piperdinyl, 3-piperdinyl or 3-pyrrolidinyl groups may be substituted on the piperindinyl or pyrrolidinyl nitrogen with a group $R^9$ which can be, for example, —C(O)N($R^{10}$)$_2$, —CH$_2$C(O)N($R^{10}$)$_2$, —SO$_2R^{10}$, —SO$_2$N($R^{10}$)$_2$, —C(O)$R^{11}$, —C(O)O$R^{11}$, alkyl, aryl, aralkyl, cycloalkyl, heterocycloalkyl or heteroaryl; each $R^{10}$ independently represents H, alkyl, aryl, or aralkyl (e.g., benzyl); and $R^{11}$ is alkyl, aryl, aralkyl, heteroaxyl or heterocycloalkyl.

Those skilled in the art will appreciate that compounds of formula 1.0 include compounds of formulas 1.3 and 1.4:

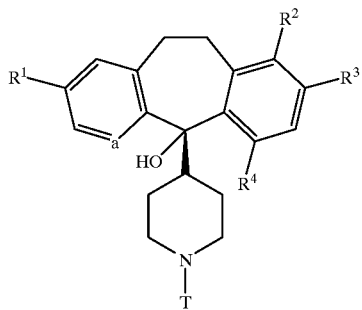

(1.3)

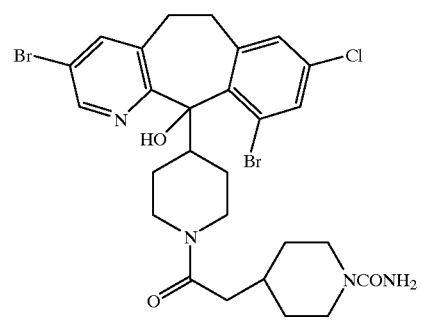

(1.4)

with compounds of 1.3 being preferred for compounds of formula 1.1, and with compounds of Formula 1.4 being preferred for compounds of formula 1.2.

Thus, compounds of the invention include compounds of the formulas:

(1.5)

(1.6)

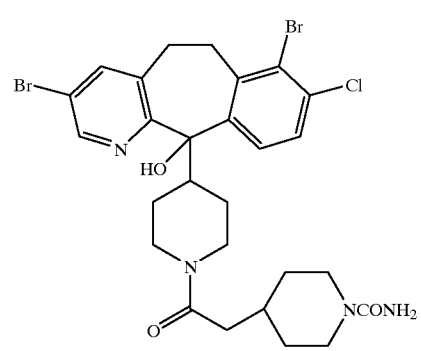

(1.7)

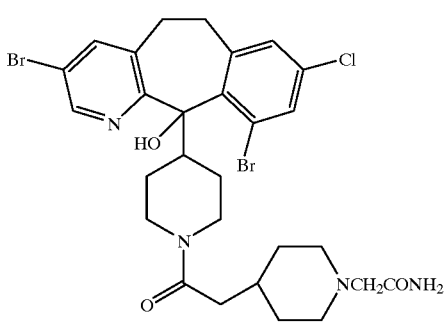

(1.8)
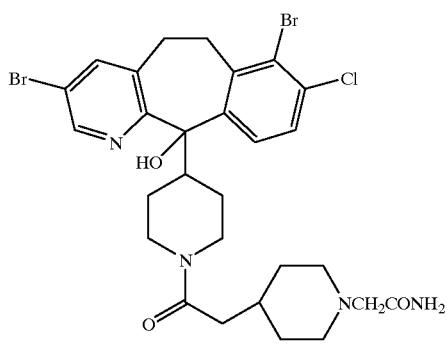

(1.9)
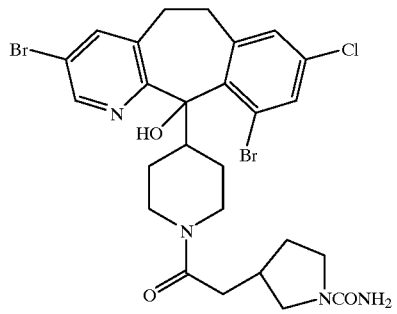

(1.10)
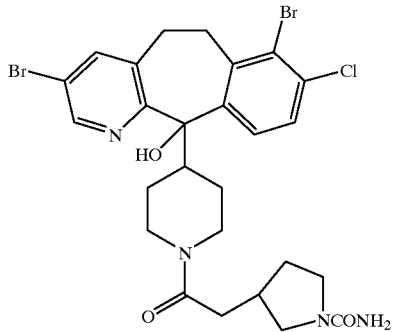

(1.11)
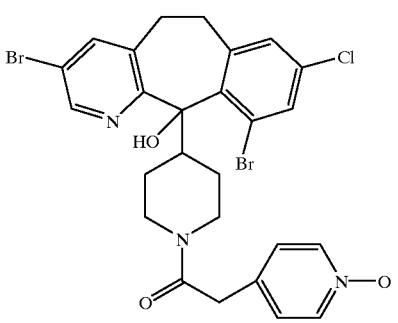

(1.12)
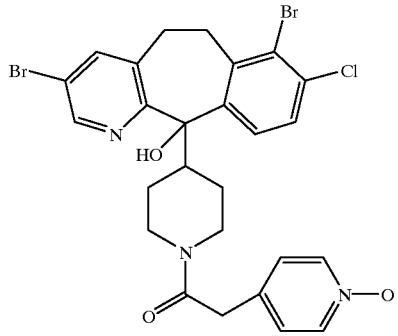

(1.13)
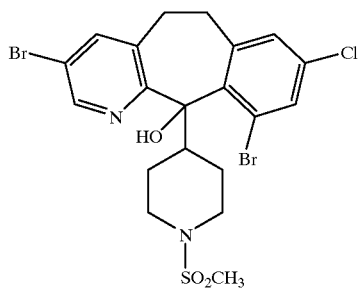

1.14
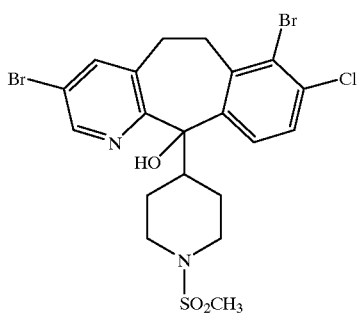

Certain compounds of the invention may exist in different isomeric (e.g., enantiomers and diastereoisomers) forms. The invention comtemplates all such isomers both in pure form and in admixture, including racemic mixtures. Enol forms are also included.

Certain compounds of formula 1.0 will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of formula 1.0 also form pharmaceutically acceptable salts, e.g., acid addition salts. For example, the pyrido-nitrogen atoms may form salts with strong acid, while compounds having basic substituents such as amino groups also form salts with weaker acids.

Examples of suitable acids for salt formation are hydrochloric, sulfuric, phosphoric, acetic, citric, oxalic, malonic, salicylic, malic, fumaric, succinic, ascorbic, maleic, methane-sulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Intermdiates useful in the preparation of the compounds of the invention may be prepared according to the procedures described in WO 95/10516 published Apr. 20, 1995, in WO 96/30363 published Oct. 3, 1996, in U.S. Pat. No. 5,151,423 and by the methods described below.

Compounds of the invention can be prepared according to the reaction:

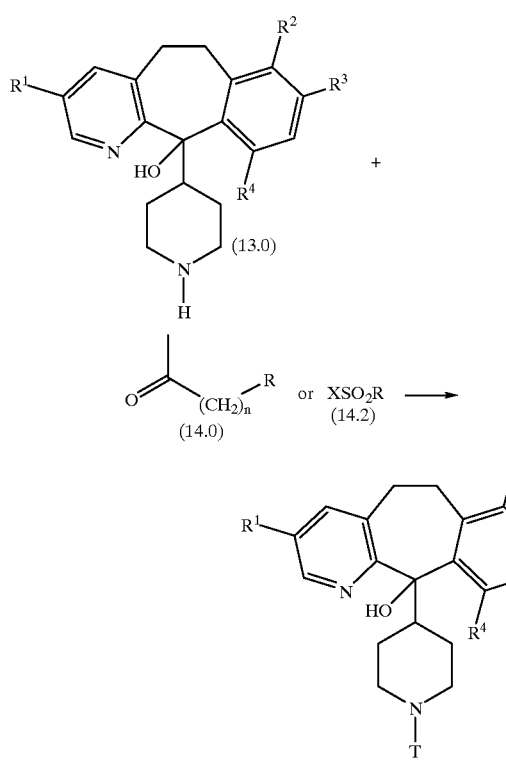

When T is $SO_2R$, X is halo, preferably, chloro.

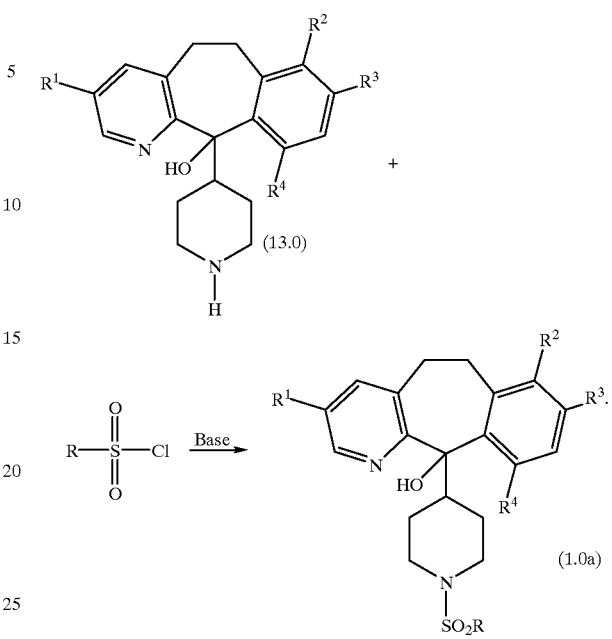

The tricyclic piperadine compound is dissolved in an appropriate solvent such as DMF of ThFF. A base is added such as triethylamine, and the appropriate alkylsuffonylchloride, prepared by methods known in the art, is added to the reaction mixture at 0° C. to ambient temperature with stirring. After 1–24 hours, the reaction mixture is added to water and the product extracted with a suitable solvent such as ethylacetate. The crude reaction product can then be chromatographed on a silica gel column.

Alkylaminosulfonamido derivatives can be prepared similarly:

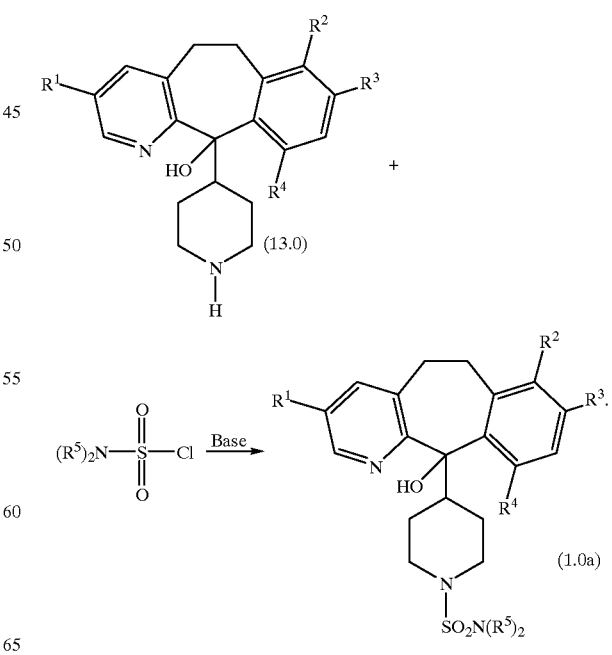

In the reaction, the carboxylic acid (14.0) is coupled to the tricyclic amine (13.0) using amide bond forming conditions well known to those skilled in the art. The substituents are as defined for Formula 1.0. For example, carbodiimide coupling methods (e.g., DEC) can be used. For example, the carboxylic acid (14.0) can be reacted with the tricyclic amine (13.0) using DEC/HOBT/NMM in DMF at about 25° C. for a sufficient period of time, e.g., about 18 hours, to produce a compound of Formula 1.0.

wherein the $R^5$ groups may be the same or different and each is as defined above. In this reaction, the tricyclic piperadine compound is dissolved in an appropriate solvent such as DMF of THF. A base is added such as triethylamine, and the appropriate alkylaminosulfonylchloride, prepared by methods known in the art, is added to the reaction mixture at 0° C. to ambient temperature with stirring. After 1–24 hours, the reaction mixture is added to water and the product extracted with a suitable solvent such as ethylacetate. The crude reaction product can then be chromatographed on a silica gel column.

The carboxylic acids (14.0) and the sulfonates (14.2) are generally known in the art or can be prepared by methods well known in the literature.

Compounds of Formula 13.0 can be prepared from compounds of formula 13.0a:

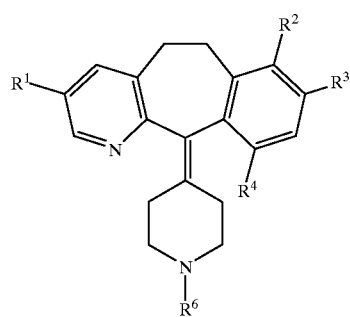

(13.0a)

wherein $R^6$ is H, alkyl, carboalkoxy or any other group that can be converted into a group T. The compounds of formula 13.0a are prepared by methods known in the art, for example, by methods disclosed in WO 95/10516, in WO 96/30363 published Oct. 3, 1996, in U.S. Pat. No. 5,151,423 and those described below.

The double bond in the compounds of formula 13.0a can be cleaved by oxidation, e.g., by the method in Preparative Example 3 below, to give the ketones of formula 15.0 below:

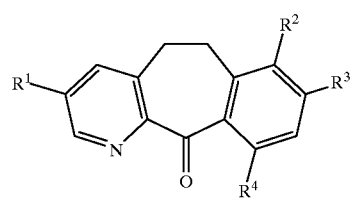

15.0

Compounds of Formula 13.0a wherein the C-3 postion of the pyridine ring in the tricyclic structure is substituted by bromo (i.e., $R^1$ is Br) can also be prepared by a procedure comprising the following steps:

(a) reacting an amide of the formula:

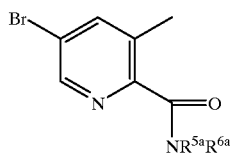

wherein $R^{5a}$ is hydrogen and $R^{6a}$ is $C_1$–$C_6$ alkyl, aryl or heteroaryl; $R^{5a}$ is $C_1$–$C_6$ alkyl, aryl or heteroaryl and $R^{6a}$ is hydrogen; $R^{5a}$ and $R^{6a}$ are independently selected from the group consisting of $C_1$–$C_6$ alkyl and aryl; or $R^{5a}$ and $R^{6a}$, together with the nitrogen to which they are attached, form a ring comprising 4 to 6 carbon atoms or comprising 3 to 5 carbon atoms and one hetero moiety selected from the group consisting of —O— and —$NR^{9a}$—, wherein $R^{9a}$ is H, $C_1$–$C_6$ alkyl or phenyl;

with a compound of the formula:

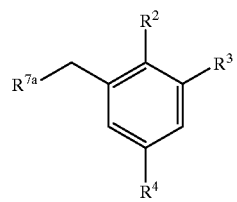

wherein $R^2$, $R^3$, and $R^4$ are as defined above and $R^{7a}$ is Cl or Br, in the presence of a strong base to obtain a compound of the formula:

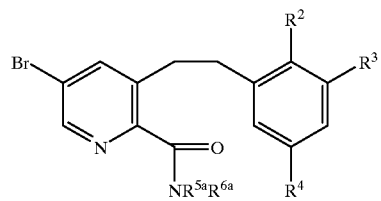

(b) reacting a compound of step (a) with $POCl_3$ to obtain a cyano compound of the formula:

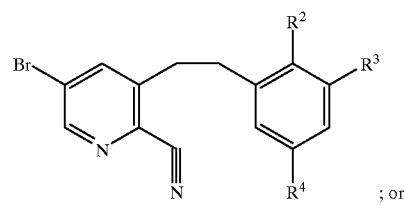

; or (c) reacting the cyano compound with a piperidine derivative of the formula:

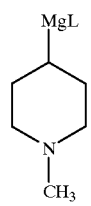

wherein L is halo selected from the group consisting of Cl and Br, to obtain a ketone of the formula below:

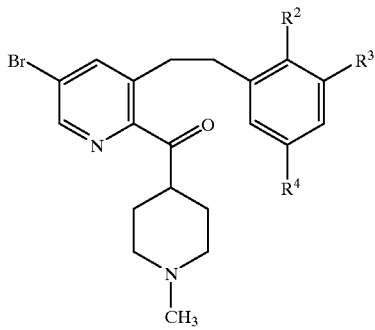

(d)(i) cyclizing the ketone under acid conditions (e.g., aluminum chloride, triflic acid, or sulfuric acid) to obtain a compound of Formula 13.0a wherein $R^6$ is methyl, which can be cleaved to give the compound of formula 15.0, Methods for preparing compounds of Formula 13.0a disclosed in WO 95/10516, in WO 96/30363 published Oct. 3, 1996, in U.S. Pat. No. 5,151,423 and described below employ a tricyclic ketone intermediate. Such intermediates of the formula:

15.0

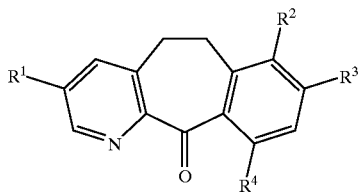

wherein $R^1$, $R^2$, $R^3$ and $R^4$ are as defined above, can be prepared by the following process comprising:

(a) reacting a compound of the formula:

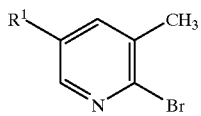

(i) with an amine of the formula $NHR^{5a}R^{6a}$, wherein $R^{5a}$ and $R^{6a}$ are as defined in the process above; in the presence of a palladium catalyst and carbon monoxide to obtain an amide of the formula:

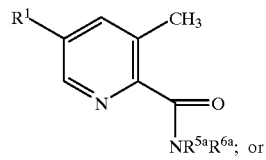

(ii) with an alcohol of the formula $R^{10a}OH$, wherein $R^{10a}$ is $C_1$–$C_6$ lower alkyl or $C_3$–$C_6$ cycloalkyl, in the presence of a palladium catalyst and carbon monoxide to obtain the ester of the formula:

followed by reacting the ester with an amine of formula $NHR^{5a}R^{6a}$ to obtain the amide;

(b) reacting the amide with an iodo-substituted benzyl compound of the formula:

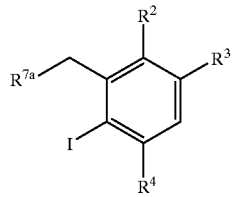

wherein $R^2$, $R^3$, $R^4$ and $R^{7a}$ are as defined above, in the presence of a strong base to obtain a compound of the formula:

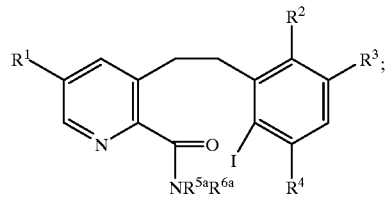

and (c) cyclizing a compound of step (b) with a reagent of the formula $R^{8a}MgL$, wherein $R^{8a}$ is $C_1$–$C_8$ alkyl, aryl or heteroaryl and L is Br or Cl, provided that prior to cyclization, compounds wherein $R^{5a}$ or $R^{6a}$ is hydrogen are reacted with a suitable N-protecting group.

Compounds of Formula 1.0 wherein substituent a is NO (Ring I) can be made from compounds of Formula 13.0a using procedures well known to those skilled in the art. For example, the compound of Formula 13.0a can be reacted with m-chloroperoxybenzoic acid in a suitable organic solvent, e.g., dichloromethane (usually anhydrous) or methylene chloride, at a suitable temperature, to produce a compound of Formula 13.0b:

(13.0b)

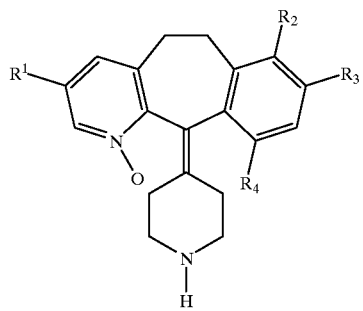

which can then be cleaved to provide a compound of formula 15.0 above.

Generally, the organic solvent solution of Formula 13.0a is cooled to about 0° C. before the m-chloroperoxybenzoic acid is added. The reaction is then allowed to warm to room temperature during the reaction period. The desired product can be recovered by standard separation means. For example, the reaction mixture can be washed with an aqueous solution of a suitable base, e.g., saturated sodium bicarbonate or NaOH (e.g., 1 N NaOH), and then dried over anhydrous magnesium sulfate. The solution containing the product can be concentrated in vacuo. The product can be purified by standard means, e.g., by chromatography using silica gel (e.g., flash column chromatography).

Alternatively, compounds of Formula 1.0, wherein substituent a is NO, can be made from compounds of Formula 1.0, wherein substituent a is N, by the m-chloroperoxybenzoic acid oxidation procedure described above.

Those skilled in the art will appreciate that it is preferable to avoid an excess of m-chloroperoxybenzoic acid when the oxidation reaction is carried out on the compounds of formula 13.0a. In these reactions an excess of m-chloroperoxybenzoic can cause oxidation of the C-11 double bond.

Compounds of formula 1.0 wherein Z is S can be prepared from compounds of formula 1.0 wherein Z is O by treatment with a suitable sulfur transfer reagent such as Lawsson's reagent.

Compounds of the invention having asymmetric carbons (e.g., compounds of the invention wherein X is CH or N have an asymmetric carbon at. the C-11 position of the the tricyclic ring) can be separated into enantiomers by techniques known in the art, e.g., by chiral salt resolution or by chiral HPLC.

Compounds useful in this invention are exemplified by the following examples, which should not be construed to limit the scope of the disclosure.

Preparative Example 1

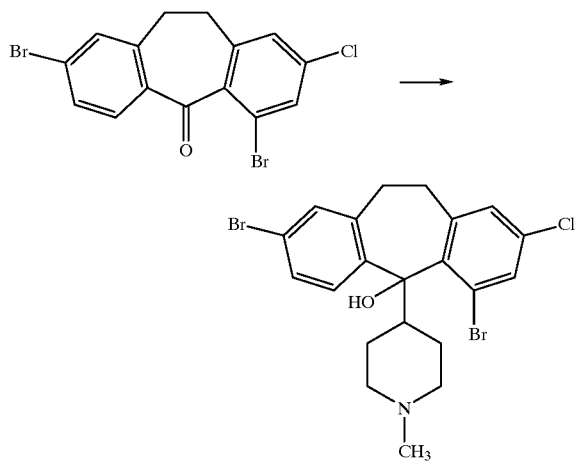

3,10-dibromo-8-chloro-6,11-dihydro-11-one-5 H-benzol [5,6]-cycloheptyl-[1,2-b]pyridine (2 gm, 4.98 mmol) was dissolved in 20 ml of dry tetrahydrofuran under a dry nitrogen atmosphere. 5 ml of a 1.5 molar solution of N-methyl-piperidine-4-magnesium chloride was added and the reaction stirred for 18 hours. The reaction mixture was washed with saturated ammonium chloride, dried over magnesium sulfate, filtered and evaporated to a brown oil which was chromatographed on silica gel using 2.5% methanol/ methylene chloride as the eluent to obtain 2.11 gm, 85% of 3,10-dibromo-8-chloro-6,11-dihydro-11-(1-methyl-4-piperidinyl) -5 H-benzo[5,6]cycloheptyl[1,2-b]pyridin-11-ol. FABMS (M+H)=501

Preparative Example 2

Step A:

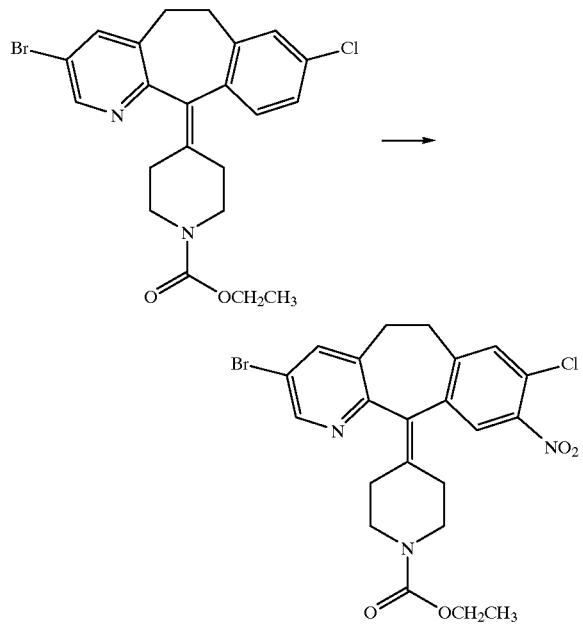

Combine 25.86 g (55.9 mmol) of 4-(8-chloro-3-bromo-5,6-dihydro-11 H-benzo[5,6]cyclohepta[1,2-b]pyridin-11-ylidene)-1-piperidine-1-carboxylic acid ethyl ester and 250 mL of concentrated $H_2SO_4$ at −5° C., then add 4.8 g (56.4 mmol) of $NaNO_3$ and stir for 2 hours. Pour the mixture into 600 g of ice and basify with concentrated $NH_4OH$ (aqueous). Filter the mixture, wash with 300 mL of water, then extract with 500 mL of $CH_2Cl_2$. Wash the extract with 200 mL of water, dry over $MgSO_4$, then filter and concentrate in vacuo to a residue. Chromatograph the residue (silica gel, 10% EtOAc/$CH_2Cl_2$) to give 24.4 g (86% yield) of the product. m.p. =165–167° C., Mass Spec.: $MH^+$=506 (CI). Elemental analysis: calculated −C, 52.13; H, 4.17; N, 8.29; found −C, 52.18; H, 4.51; N. 8.16.

Step B:

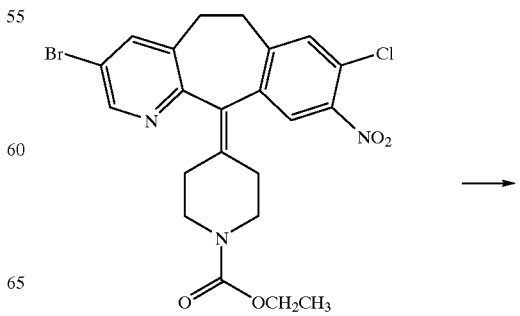

-continued

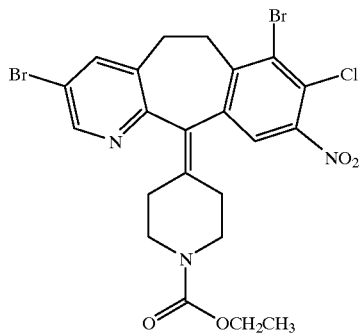

Combine 20 g (40.5 mmol) of the product of Step A and 200 mL of concentrated $H_2SO_4$ at 20° C., then cool the mixture to 0° C. Add 7.12 g (24.89 mmol) of 1,3-dibromo-5,5-dimethyl-hydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated $NH_4OH$ (aqueous) at 0° C., and collect the resulting solid by filtration. Wash the solid with 300 mL of water, slurry in 200 mL of acetone and filter to provide 19.79 g (85.6% yield) of the product. m.p. =236–237° C., Mass Spec.: $MH^{30}$ =584 (CI). Elemental analysis: calculated –C, 45.11; H, 3.44; N, 7.17; found –C, 44.95; H, 3.57; N, 7.16

Step C:

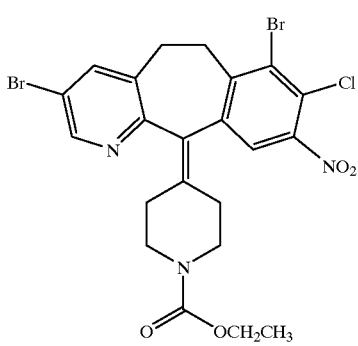

Combine 25 g (447 mmol) of Fe filings, 10 g (90 mmol) of $CaCl_2$ and a suspension of 20 g (34.19 mmol) of the product of Step B in 700 mL of 90:10 EtOH/water at 50° C. Heat the mixture at reflux overnight, filter through Celhte® and wash the filter cake with 2×200 mL of hot EtOH. Combine the filtrate and washes, and concentrate in vacuo to a residue. Extract the residue with 600 mL of $CH_2Cl_2$, wash with 300 mL of water and dry over $MgSO_4$. Filter and concentrate in vacuo to a residue, then chromatograph (silica gel, 30% EtOAc/$CH_2Cl_2$) to give 11.4 g (60% yield) of the product. m.p.=211–212° C., Mass Spec.: $MH^+554$ (CI). Elemental analysis: calculated –C, 47.55; H, 3.99; N, 7.56; found –C, 47.45; H, 4.31; N, 7.49.

Step D:

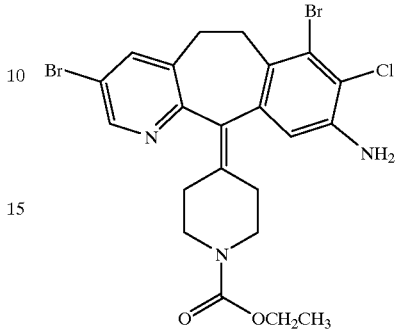

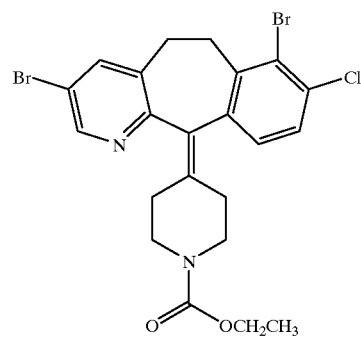

Slowly add (in portions) 20 g (35.9 mmol) of the product of Step C to a solution of 8 g (116 mmol) of $NaNO_2$ in 120 mL of concentrated HCl (aqueous) at –10° C. Stir the resulting mixture at 0° C. for 2 hours, then slowly add (dropwise) 150 mL (1.44 mole) of 50% $H_3PO_2$ at 0° C. over a 1 hour period. Stir at 0° C. for 3 hours, then pour into 600 g of ice and basify with concentrated $NH_4OH$ (aqueous). Extract with 2×300 mL of $CH_2Cl_2$, dry the extracts over $MgSO_4$, then filter and concentrate in vacuo to a residue. Chromatograph the residue (silica gel, 25% EtOAc/hexanes) to give 13.67 g (70% yield) of the product. m.p. =163–165° C., Mass Spec.: $MH^+$=539 (CI). Elemental analysis: calculated –C, 48.97; H, 4.05; N, 5.22; found –C, 48.86; H, 3.91; N, 5.18.

Step E:

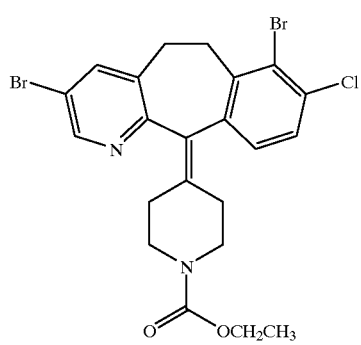

-continued

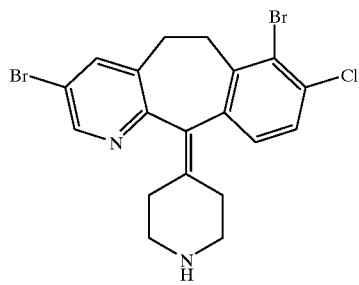

Combine 6.8 g (12.59 mmol) of the product of Step D and 100 mL of concentrated HCl (aqueous) and stir at 85° C. overnight. Cool the mixture, pour it into 300 g of ice and basify with concentrated NH$_4$OH (aqueous). Extract with 2×300 mL of CH$_2$Cl$_2$, then dry the extracts over MgSO$_4$. Filter, concentrate in vacuo to a residue, then chromatograph (silica gel, 10% MeOH/EtOAc+2% NH$_4$OH (aqueous)) to give 5.4 g (92% yield) of the title compound. m.p.= 172–174° C., Mass Spec.: MH$^+$=467 (FAB). Elemental analysis: calculated –C, 48.69; H, 3.65; N, 5.97; found –C, 48.83; H, 3.80; N, 5.97

Preparative Example 3

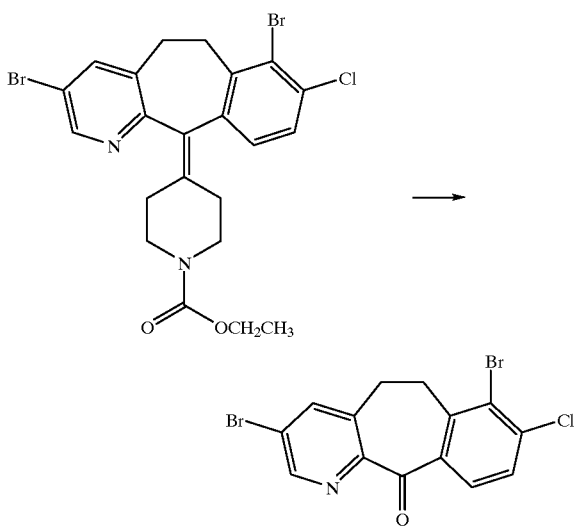

Combine 16.6 g (0.03 mole) of the product of Preparative Example 3, Step D, with a 3:1 solution of CH$_3$CN and water (212.65 mL CH$_3$CN and 70.8 mL of water) and stir the resulting slurry overnight at room temperature. Add 32.833 g (0.153 mole) of NaIO$_4$ and then 0.31 g (2.30 mmol) of RuO$_2$ and stir at room temperature give 1.39 g (69% yield) of the product. (The addition of RuO is accompanied by an exothermic reaction and the temperature climbs from 20° to 30° C.) Stir the mixture for 1.3 hrs. (temperature returned to 25° C. after about 30 min.), then filter to remove the solids and wash the filtrate with CH$_2$Cl$_2$. Concentrate the filtrate in vacuo to a residue and dissolve the residue in CH$_2$Cl$_2$. Filter to remove insoluble solids and wash the solids with CH$_2$Cl$_2$. Wash the filtrate with water, concentrate to a volume of about 200 mL and wash with bleach, then with water. Extract with 6 N HCl (aqueous). Cool the aqueous extract to 0° C. and slowly add 50% NaOH (aqueous) to adjust to pH =4 while keeping the temperature <30° C. Extract twice with CH$_2$Cl$_2$, dry over MgSO$_4$ and concentrate in vacuo to a residue. Slurry the residue in 20 mL of EtOH and cool to 0° C. Collect the resulting solids by filtration and dry the solids in vacuo to give 7.95 g of the product. $^1$H NMR (CDCl$_3$, 200 MHz): 8.7 (s, 1 H); 7.85 (m, 6 H); 7.5 (d, 2 H); 3.45 (m, 2 H): 3.15 (m, 2 H).

Preparative Example 4

Step A:

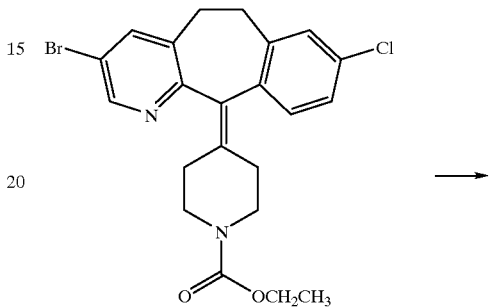

Combine 15 g (38.5 mmol) of 4-(8-chloro-3-bromo-5,6-dihydro-11 H-benzo[5,6]cyclohepta[1,2-b]pyridin-11-ylidene)-1-piperidine-1-carboxylic acid ethyl ester and 150 mL of concentrated H$_2$SO$_4$ at −5° C., then add 3.89 g (38.5 mmol) of KNO$_3$ and stir for 4 hours. Pour the mixture into 3 L of ice and basify with 50% NaOH (aqueous). Extract with CH$_2$Cl$_2$, dry over MgSO$_4$, then filter and concentrate in vacuo to a residue. Recrystallize the residue from acetone to give 6.69 g of the product. 1H NMR (CDCl$_3$, 200 MHz): 8.5 (s, 1 H); 7.75 (s, 1 H); 7.6 (s, 1 H); 7.35 (s, 1 H); 4.15 (q, 2 H); 3.8 (m, 2 H); 3.5–3.1 (m, 4 H); 3.0–2.8 (m, 2 H); 2.6–2.2 (m, 4 H); 1.25 (t, 3 H).

Step B:

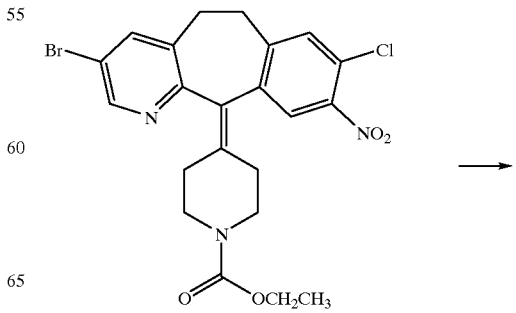

-continued

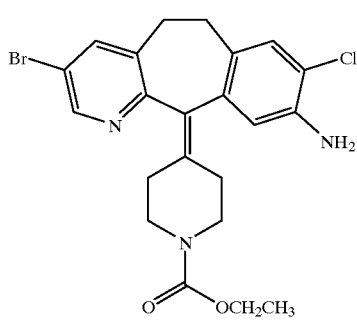

Combine 6.69 g (13.1 mmol) of the product of Step A and 100 mL of 85% EtOH/water, then add 0.66 g (5.9 mmol) of CaCl$_2$ and 6.56 g (117.9 mmol) of Fe and heat the mixture at reflux overnight. Filter the hot reaction mixture through celite® and rinse the filter cake with hot EtOH. Concentrate the filtrate in vacuo to give 7.72 g of the product. Mass Spec.: MH$^+$=478.0

Step C:

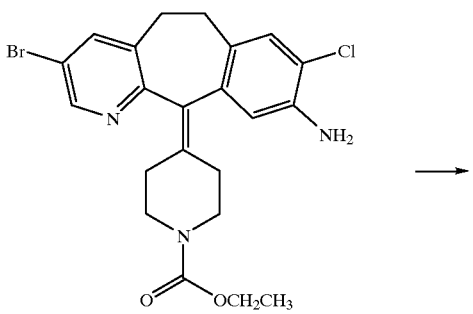

Combine 7.70 g of the product of Step B and 35 mL of HOAc, then add 45 mL of a solution of Br$_2$ in HOAc and stir the mixture at room temperature overnight. Add 300 mL of 1 N NaOH (aqueous), then 75 mL of 50% NaOH (aqueous) and extract with EtOAc. Dry the extract over MgSO$_4$ and concentrate in vacuo to a residue. Chromatograph the residue (silica gel, 20%–30% EtOAc/hexane) to give 3.47 g of the product (along with another 1.28 g of partially purified product). Mass Spec.: MH$^+$=555.9. $^1$H NMR (CDCl$_3$, 300 MHz): 8.5 (s, 1 H); 7.5 (s, 1 H); 7.15 (s, 1 H); 4.5 (s, 2 H); 4.15 (m, 3 H); 3.8 (br s, 2 H); 3.4–3.1 (m, 4 H); 9–2.75 (m, 1 H); 2.7–2.5 (m, 2 H); 2.4–2.2 (m, 2 H); 1.25 (m, 3 H).

Step D:

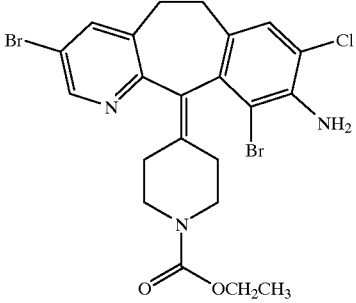

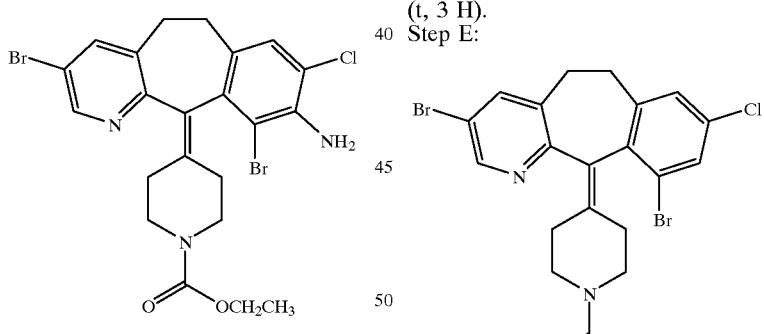

Combine 0.557 g (5.4 mmol) of t-butylnitrite and 3 mL of DMF, and heat the mixture at to 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with CH$_2$Cl$_2$, dry the extract over MgSO$_4$ and concentrate in vacuo to a residue. Chromatograph the residue (silica gel, 10%–20% EtOAc/hexane) to give 0.74 g of the product. Mass Spec.: MH$^+$=541.0.
$^1$H NMR (CDCl3, 200 MHz): 8.52 (s, 1 H); 7.5 (d, 2 H); 7.2 (s, 1 H); 4.15 (q, 2 H); 3.9–3.7 (m, 2 H); 3.5–3.1 (m, 4 H); 3.0–2.5 (m, 2 H); 2.4–2.2 (m, 2 H); 2.1–1.9 (m, 2 H); 1.26 (t, 3 H).

Step E:

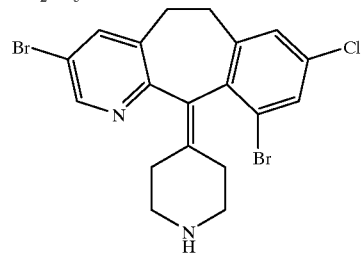

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with $CH_2Cl_2$. Dry the extract over $MgSO_4$ and concentrate in vacuo to give 0.59 g of the title compound. Mass Spec.: $M^+$=468.7. m.p.=123.9°–124.2° C.

The title compound can be cleaved by the methodology of Preparative Example 3 to prepare the corresponding 11-ketone having 3,10-dibromo-8-chloro substituents.

Preparative Example 5

Step A:

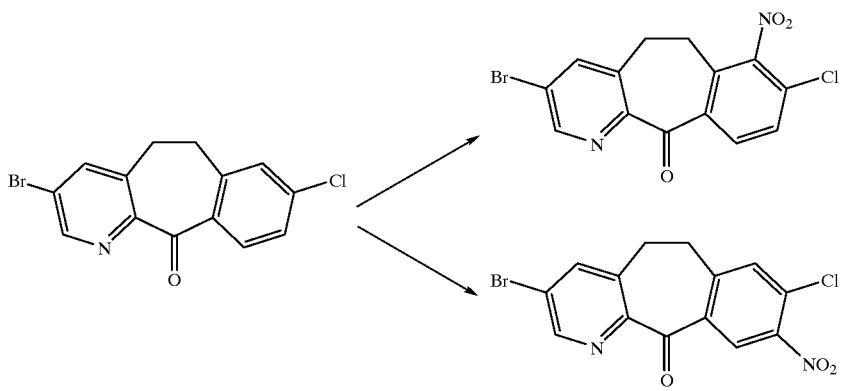

Combine 40.0 g (0.124 mole) of the starting ketone and 200 mL of $H_2SO_4$ and cool to 0° C. Slowly add 13.78 g (0.136 mole) of $KNO_3$ over a period of 1.5 hrs., then warm to room temperature and stir overnight. Work up the reaction using substantially the same procedure as described for Preparative Example 2, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds.

Step B:

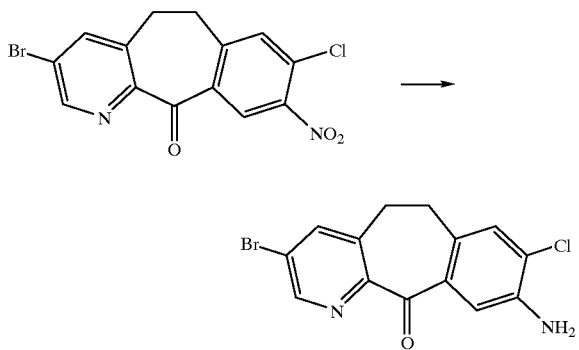

React 28 g (76.2 mmol) of the 9-nitro product of Step A, 400 mL of 85% EtOH/water, 3.8 g (34.3 mmol) of $CaCl_2$ and 38.28 g (0.685 mole) of Fe using substantially the same procedure as described for Preparative Example 2, Step C, to give 24 g of the product Step C:

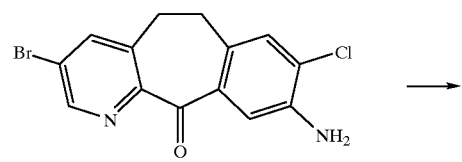

-continued

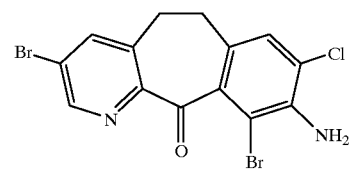

Combine 13 g (38.5 mmol) of the product of Step B, 140 mL of HOAc and slowly add a solution of 2.95 mL (57.8 mmol) of $Br_2$ in 10 mL of HOAc over a period of 20 min. Stir the reaction mixture at room temperature, then concentrate in vacuo to a residue. Add $CH_2Cl_2$ and water, then adjust to pH=8–9 with 50% NaOH (aqueous). Wash the organic phase with water, then brine and dry over $Na_2SO_4$. Concentrate in vacuo to give 11.3 g of the product.

Step D:

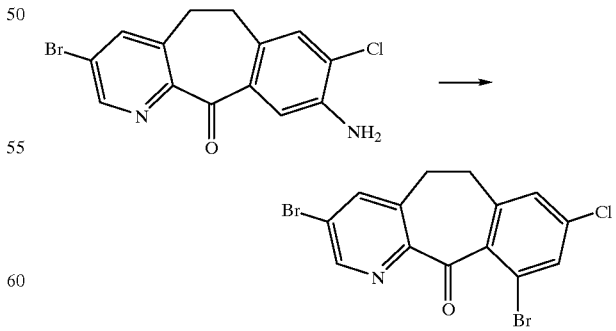

Cool 100 mL of concentrated HCl (aqueous) to 0° C., then add 5.61 g (81.4 mmol) of $NaNO_2$ and stir for 10 min. Slowly add (in portions) 11.3 g (27.1 mmol) of the product of Step C and stir the mixture at 0°–3° C. for 2.25 hrs.

Slowly add (dropwise) 180 mL of 50% H$_3$PO$_2$ (aqueous) and allow the mixture to stand at 0° C. overnight. Slowly add (dropwise) 150 mL of 50% NaOH over 30 min., to adjust to pH=9, then extract with CH$_2$Cl$_2$. Wash the extract with water, then brine and dry over Na$_2$SO$_4$. Concentrate in vacuo to a residue and chromatograph (silica gel, 2% EtOAc/CH$_2$Cl$_2$) to give 8.6 g of the product.

EXAMPLE 1

Step A

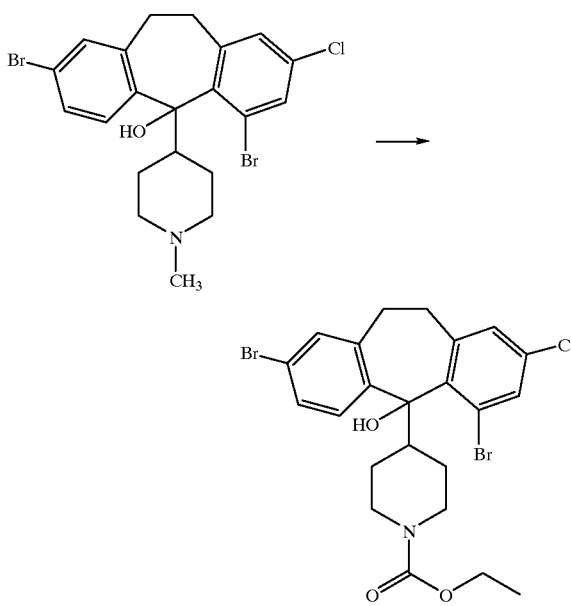

The compound from Preparative Example 1 (0.95 gm, 1.9 mmol) was dissolved in 34 ml of toluene. Triethylamine (1 ml) and ethylchloroformate (1.82 ml, 10 eq.) were added and the reaction mixture refluxed for two hours. The reaction mixture was cooled to ambient temperature and evaporated to an oil. The oil was chromatographed on silica gel using 15 to 20% ethylacetate/hexanes to obtain 0.77 gm of ethyl 4-(3,10-dibromo-8-chloro-6,11-dihydro-11-hydroxy-5 H-benzo[5,6]cyclohepta[1,2-b]pyridin-11-yl)-1-piperidinecarboxylate. FABMS (M+H)=559

Step B

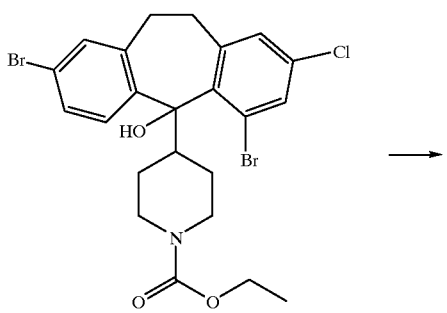

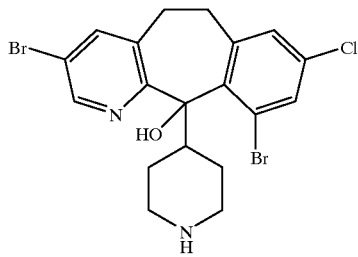

The compound from Preparative Example 2 (0.37 gm) was dissolved in 5 ml of concentrated hydrochloric acid and refluxed for 18 hours. The mixture was evaporated to a brown solid of the compound 4-(3,10-dibromo-8-chloro-6,11-dihydro-11-hydroxy-5 H-benzo[5,6]cyclohepta[1,2-b] pyridin-11-yl)-1-piperidine and used without chromatography.

Step C

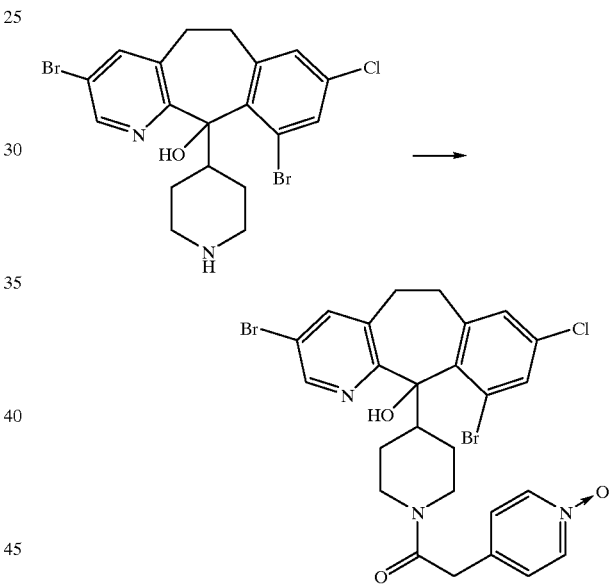

The comnpound of Preparative Example 3 (100 mg, 0.206 mmol) was dissolved in 2 ml of N,N-dimethylformamide. 4-Pyrldylacetic acid-N-oxide (126 mg, 0.82 mmol), 1-(3-dimethylaminopropyl)-3-ethylcarbodiimide hydrochloride (DEC) (0.079 mg, 0.5 mmol)), 1-hydroxybenzotriazole (HOBt) (0.056 gm, 0.5 mmol), and N-methylmorpholine ( 0.23 ml, 2.0 mmol) were added and the reaction mixture stirred at ambient temperature. After 24 hours, the reaction mixture was added to brine and extracted with 3×15 ml of ethylacetate. The combined ethylacetate washes were combined and the solvent evaporated under vacuo to give a gum. The gum was chromatographed flash silica gel using 10% methanol/methylenechloride as the eluent to obtain 0.076 gm of 4-(3,10-dibromo-8-chloro-6,11-dihydro-11-hydroxy-5 H-benzol[5,6]cyclohepta[1,2-b]pyridin-11-yl)-1-(4-pyridinylacetyl)piperidine N1-oxide. FABMS (M+H)= 622

EXAMPLE 2

Step A:

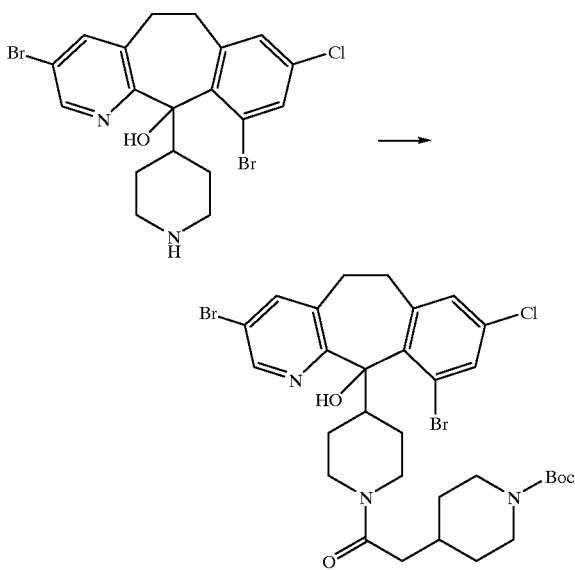

The procedure of Example 1 above was followed replacing 4-pyridylacetic acid-N-oxide with N-Boc-4-piperadineacetic acid to obtain 4-(3,10-dibromo-8-chloro-6,11-dihydro-11-hydroxy-5 H-benzo[5,6]cyclohepta[1,2-b]pyridin-11-yl)-1-(N-BOC-4-piperdinylacetyl)piperidine in 85% yield. High resolution MS: observed=712.0975

Step B:

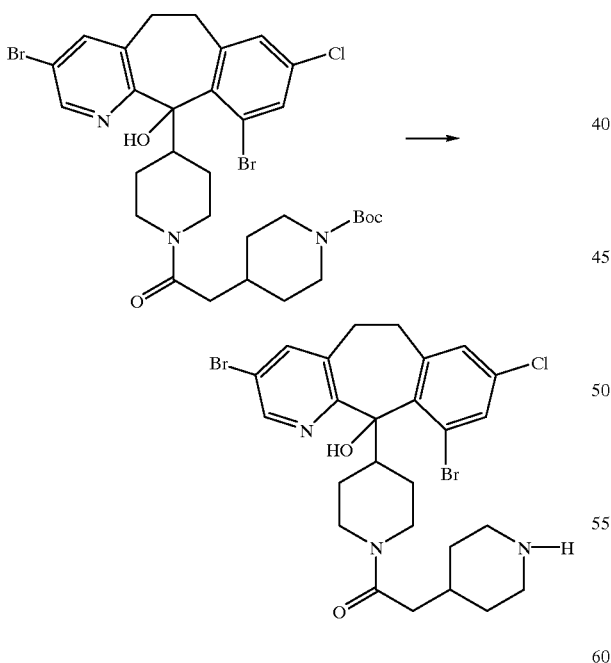

The compound of Step A above (0.21 gm) was dissolved in 50% trifluoroacetic acid/methylenechloride and stirred for 1 hour. The reaction mixture was evaporated to obtain an oil which was dissolved in 2 ml of methylenechloride to provide 4-[2-[4-(3,10-dibromo-8-chloro-6,11-dihydro-11-hydroxy-5 H-benzo[5,6]-cyclohepta[1,2-b]pyridin-11-yl)-1-piperdinyl]-2-oxoethyl]-1-piperidine.

Step C:

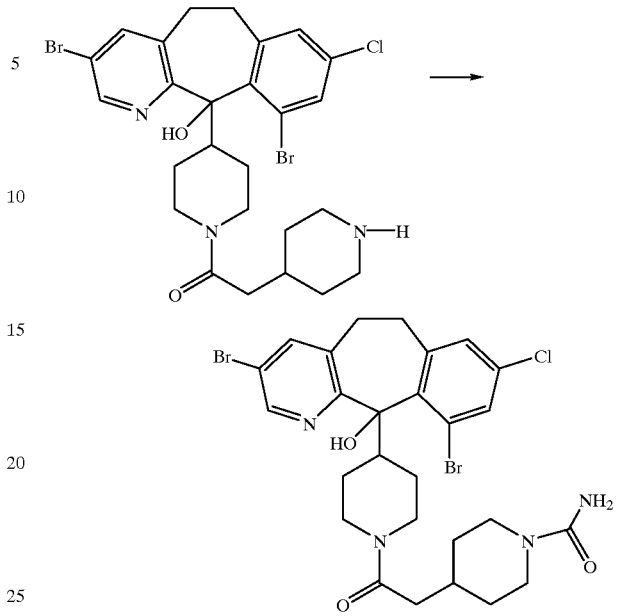

Trimethylsilylisocyanate (234 ul, 1.47 mmol) was added and the reaction mixture stirred at ambient temperature for 15 hours. The solvent was evaporated and the crude product chromatographed on silica gel using 7.5% methanol/methylenechloride to obtain 100 mg, 62% of 4-[2-[4-(3,10-dibromo-8-chloro-6,11-dihydro-11-hydroxy-5 H-benzo[5,6]cyclohepta[1,2-b]pyridin-11-yl)-1-piperdinyl]-2-oxoethyl]-1-piperidinecarboxamide. High resolution MS:observed= 655.0509

EXAMPLE 3

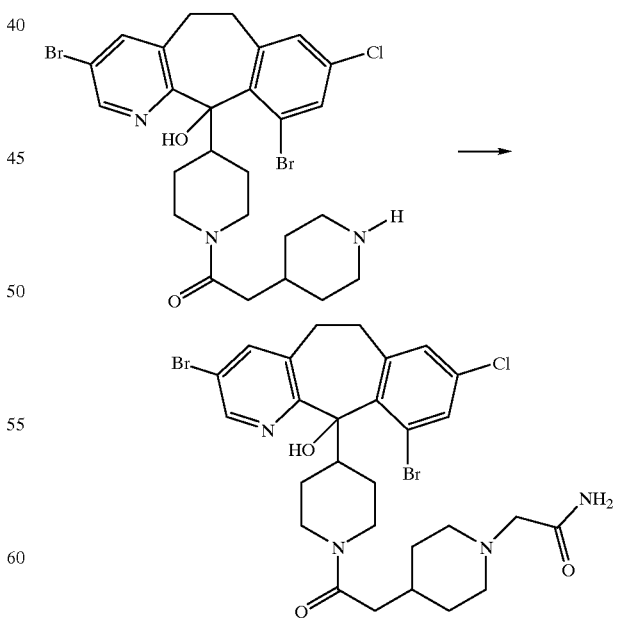

The compound of Example 2 Step A above (0.069 g, 0.113 mmol) was dissolved in 2 ml of N,N-dimethylformamide. Sodium carbonate (0.036 g, 0.34 mmol) and bromoacetamide (0.023 g, 0.17 mmol) were added and the reaction mixture stirred at ambient temperature for 24 hours. The mixture was added to brine and extracted with ethylacetate. The ethylacetate layer was dried over magnesium sulfate, filtered and evaporated to obtain a crude solid. The crude solid was chromatographed on silica gel using 5% methanol/methylenechloride to obtain 4-[2-[4-(3,10-dibromo-8-chloro-6,11-dihydro-11-hydroxy-5 H-benzo[5,6]cyclohepta-[1,2-B]pyridin-11-yl)-1-piperidinyl]-2-oxoethyl]-1-piperidineacetamide. High resolution MS:observed=669.0666

The following compounds can be prepared utilizing the procedure of Example 1 above and substituting the following carboxylic acids for 4-pyridylacetic acid-N-oxide.

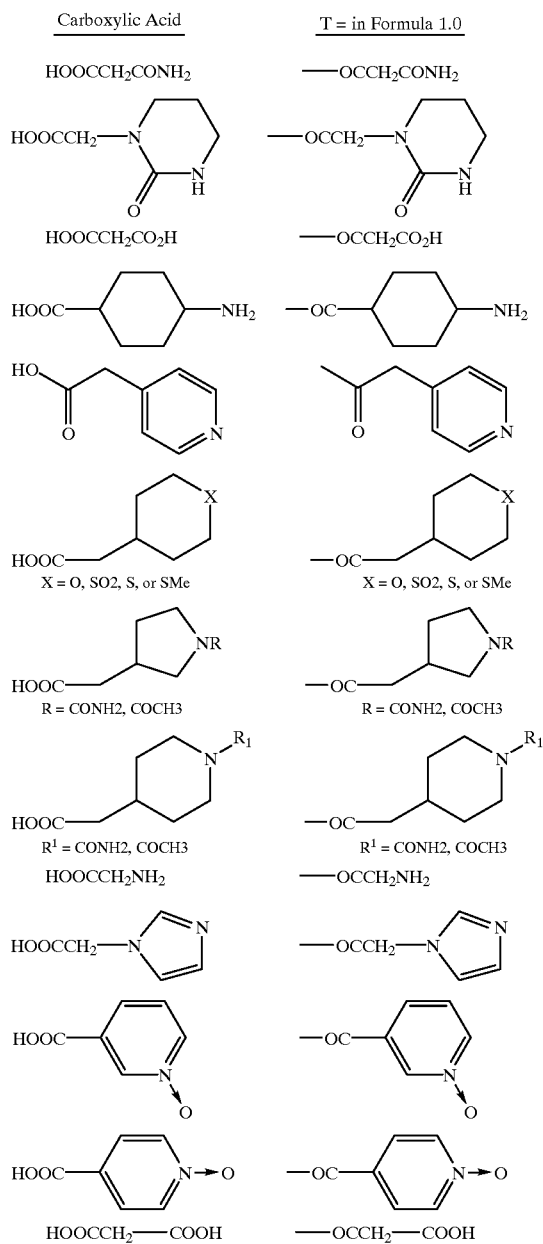

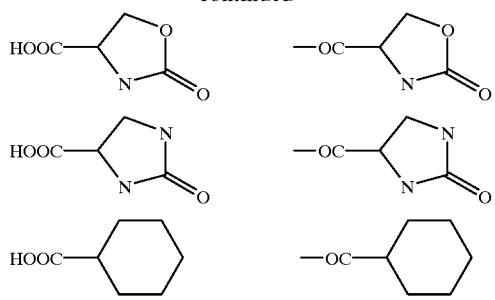

ASSAYS

FPT $IC_{50}$ (inhibition of farnesyl protein transferase, in vitro enzyme assay) and COS Cell $IC_{50}$ (Cell-Based Assay) were determined following tile assay procedures described in WO 95/10516, published Apr. 20, 1995. GGPT $IC_{50}$ (inhibition of geranylgeranyl protein transferase, in vitro enzyme assay), Cell Mat Assay, and anti-tumor activity (in vivo anti-tumor studies) could be determined by the assay procedures described in WO 95/10516. The disclosure of WO 95/10516 is incorporated herein by reference thereto.

Additional assays can be carried out by following essentially the same procedure as described above, but with substitution of alternative indicator tumor cell lines in place of the T24-BAG cells. The assays can be conducted using either DLD-1-BAG human colon carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay:

Anchorage-independent growth is a characteristic of tumorigenic cell lines. Human tumor cells are suspended in growth medium containing 0.3% agarose and an indicated concentration of a farnesyl transferase inhibitor. The solution is overlayed onto growth medium solidified with 0.6% agarose containing the same concentration of farnesyl transferase inhibitor as the top layer. After the top layer is solidified, plates are incubated for 10–16 days at 37° C. under 5% $CO_2$ to allow colony outgrowth. After incubation, the colonies are stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the $IC_{50}$'s can be determined.

Results from the in vitro enzyme assay are given in Table 1.

TABLE 1

| Example No. | Compound | FPT IC50 (μM) |
|---|---|---|
| #1 Step C | | <0.002 |
| #2 Step C | | 0.0108 |
| #2 Step A | | 0.042 |
| #3 | | 0.0087 |

TABLE 1-continued

| Example No. | Compound | FPT IC50 ($\mu$M) |
|---|---|---|
| #2 Step B | (structure shown) | 0.0125 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredients | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|   | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound selected from:

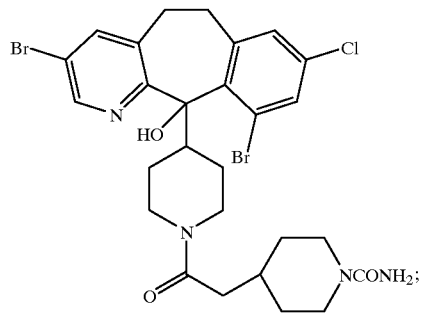
(1.5)

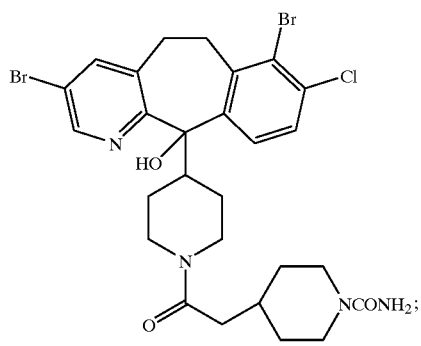
(1.6)

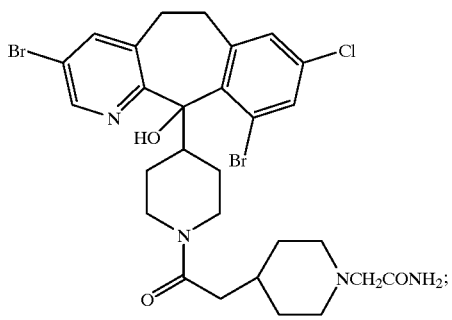
(1.7)

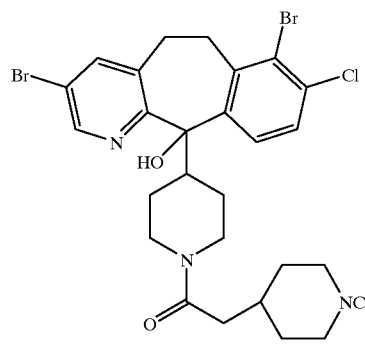
(1.8)

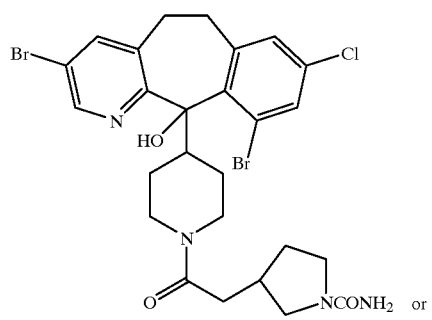
(1.9)

or

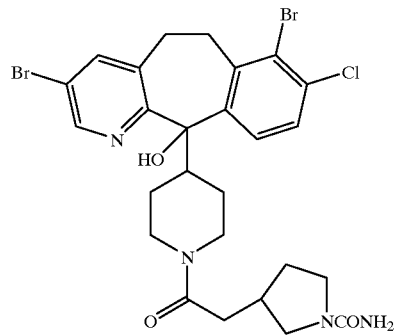
(1.10)

2. A method of treating tumor cells wherein the tumor cells treated are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, breast tumor cells and prostate tumor cells comprising administering an effective amount of a compound of claim 1.

3. A method of inhibiting farnesyl protein transferase comprising the administration of an effective amount of a compound of claim 1.

4. A pharmaceutical composition comprising an effective amount of compound of claim 1 in combination with a pharmaceutically acceptable carrier.

* * * * *